United States Patent [19]

Daly et al.

[11] Patent Number: 5,314,899
[45] Date of Patent: May 24, 1994

[54] EPIBATIDINE AND DERIVATIVES, COMPOSITIONS AND METHODS OF TREATING PAIN

[75] Inventors: John W. Daly, Washington, D.C.; Thomas F. Spande, Bethesda; Hugo M. Garraffo, Rockville, both of Md.

[73] Assignee: The United States of America as represented by the Secretary of the Department of Health and Human Services, Washington, D.C.

[21] Appl. No.: 845,042

[22] Filed: Mar. 3, 1992

[51] Int. Cl.$^5$ .................. C07D 401/04; A61K 31/44
[52] U.S. Cl. ........................ 514/339; 546/272; 548/466; 548/452; 548/312.1; 544/405; 544/333; 514/413; 514/397; 514/253; 514/256
[58] Field of Search .............. 546/272; 548/452; 514/339

[56] References Cited

U.S. PATENT DOCUMENTS 4,499,099 2/1985 Watts .................. 548/452
5,015,655 5/1991 Galliani et al. .......... 548/452

OTHER PUBLICATIONS

Fraser et al. Canadian Jour. of Chem. vol. 48. 1970 pp. 2065-2074.
Kricka et al. Advances in Heterocyclic Chemistry vol. 16. pp. 87-121. 1974.
Aceto et al. Problems of Drug Dependence, 1992: Proceedings of the 54th Annual Scientific Meeting. pp. 460-516.

*Primary Examiner*—Jane T. Fan
*Attorney, Agent, or Firm*—Leydig, Voit & Mayer, Ltd.

[57] ABSTRACT

The present invention is directed to compounds, compositions and methods of treating pain, and derivatives that have potent analgetic activity. The compounds have the formula:

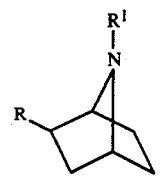

wherein $R^1$ is selected from H, lower alkyl, $C_3$-$C_9$ cycloalkyl, acyl, and $C_3$-$C_9$ cycloalkylalkyl, haloalkyl, alkenyl, alkynyl, hydroxyalkyl, or $C_3$-$C_8$ cycloalkenyl or $C_3$-$C_8$ cycloalkynyl; and wherein R is selected from cycloalkyl, aryl, heteroaryls (selected from the group consisting of pyridyl, thienyl, furanyl, imidazolyl, pyrazinyl, and pyrimidyl) or phenoxy and wherein said R groups can be substituted with hydroxyl, $C_1$-$C_6$ lower alkyl, $C_2$-$C_6$ alkenyl, $C_1$-$C_6$ lower alkoxyl, halo, $C_1$-$C_6$ haloalkyl, amino, $C_1$-$C_6$ alkylamino and $C_2$-$C_{10}$ dialkylamino, and sulfonamido or a pharmaceutically acceptable salt thereof.

7 Claims, No Drawings

EPIBATIDINE AND DERIVATIVES, COMPOSITIONS AND METHODS OF TREATING PAIN

FIELD OF THE INVENTION

The present invention is directed to epibatidine and its derivatives, compositions and methods of treating pain.

BACKGROUND OF THE INVENTION

The control of pain is at present primarily through the use of opioid-like analgetics, such as morphine, fentanyl, pentazocine, etc., or through non-steroidal antiinflammatories. There are limitations to the usefulness of such agents, and other classes of analgetics for the control and amelioration of pain are needed. A trace alkaloid epibatidine from skins of a neotropical frog is two-hundred fold more potent than morphine administered subcutaneously to mice in a standard analgetic test. In addition the analgesia elicited by epibatidine is not antagonized by the opioid antagonist naloxone, indicating that the analgesia is not due to actions of epibatidine at opioid receptors. In support of this conclusion is the very low affinity of epibatidine for dihydromorphine binding sites in rodent brain membranes. Epibatidine at higher doses causes a marked Straub-tail response, as does morphine, an effect linked to activation of dopamine pathways in the spinal cord. However, the Straub-tail response to epibatidine, unlike the Straub tail response to morphine, is not blocked by the opioid-antagonist naloxone.

SUMMARY OF THE INVENTION

The present invention is directed to a purified and isolated compound having the formula:

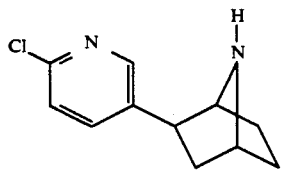

or a pharmaceutically acceptable salt thereof.

The present invention is also directed to a compound having the formula:

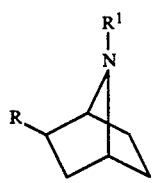

wherein $R^1$ is selected from H, lower alkyl, $C_3-C_9$ cycloalkyl, acyl, and $C_3-C_9$ cycloalkylalkyl, haloalkyl, alkenyl, alkynyl, hydroxyalkyl, or $C_3-C_8$ cycloalkenyl or $C_3-C_8$ cycloalkynyl; and wherein R is selected from cycloalkyl, aryl, heteroaryls (selected from the group consisting of pyridyl, thienyl, furanyl, imidazolyl, pyrazinyl, and pyrimidyl) or phenoxy and wherein said R groups can be substituted with hydroxyl, $C_1-C_6$ lower alkyl, $C_2-C_6$ alkenyl, $C_1-C_6$ lower alkoxyl, halo, $C_1-C_6$ haloalkyl, amino, $C_1-C_6$ alkylamino and $C_2-C_{10}$ dialkylamino, and sulfonamido or a pharmaceutically acceptable salt thereof with the proviso that R is not 6-chloro-3-pyridyl and $R^1$ is not H.

The present invention is also directed to analgetic compositions which comprise an effective amount of the above compounds, and a pharmaceutically acceptable carrier and a method for treating analgesia which comprises administering to a host in need thereof a analgetic effective amount of the compounds described above.

Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

The term "pharmaceutically-acceptable salts" embraces commonly used alkali metal salts and addition salts of free acids or free bases. Since the compounds contain basic nitrogen atoms, such salts are typically acid addition salts, or quaternary ammonium salts with one or more $C_1-C_6$ alkyl or cycloalkyl groups.

DETAILED DESCRIPTION OF THE PREFERRED EMBODIMENTS

Where the term "alkyl" is used, either alone or within other terms, such as "haloalkyl" and "hydroxyalkyl", the term "alkyl" embraces linear or branched radicals having one to about twenty carbon atoms or, preferably, one to about ten carbon atoms.

By lower alkyl, straight or branched, is meant structured monovalent radicals having from 1 to 6 carbon atoms. Examples of lower alkyl include, but are not limited to, methyl, ethyl, n-propyl, isopropyl, n-butyl, isobutyl, sec-butyl, tertiary-butyl, n-pentyl, iso-pentyl, methylbutyl, dimethylbutyl, neopentyl and n-hexyl.

By cycloalkyl is meant radicals originating from cycloalkanes having from 3 to 8 carbon atoms. Examples of cycloalkyls, include, but are not limited to, cyclopropyl, cyclobutyl, cyclopentyl and cyclohexyl. The cycloalkyl groups can be further substituted with a halogen atom such as bromine, fluorine or chlorine.

By cycloalkylalkyl is meant radicals originating from an alkane of 1 to 6 carbon atoms and which are further substituted by cycloalkyls having 3 to 8 carbon atoms. Examples of cycloalkylalkyl include, but are not limited to, cyclopropylmethyl, cyclobutylmethyl, 1-cyclopentylethyl, cyclohexylmethyl, 2-cyclohexylethyl and 3-cyclohexylpropyl.

By acyl is meant an organic radical derived from an organic acid by the removal of the hydroxyl group, i.e., a radical having the formula $R^2C(O)-$, wherein $R^2$ is a lower $C_1-C_6$ alkyl, $C_3-C_7$ cycloalkyl, a phenyl, a benzyl or phenethyl group. Examples of acyl groups, include, but are not limited to, formyl, acetyl, propionyl and butyryl.

By arylacyl is meant an acyl group as described above wherein $R^2$ is an aromatic radical, i.e., phenyl and naphthyl. The aromatic radical can be further substituted by $C_1-C_6$ lower alkyl, halogen, lower haloalkyl, lower mono-and di-alkylamino and sulfonamido groups.

By lower haloalkyl is meant a $C_1-C_6$ alkyl radical which is substituted with one or more, same or different, halogen atoms selected from the group consisting of bromine, chlorine and fluorine and preferred are mono- or di-halo substituted $C_1-C_6$ alkyl. Examples of lower haloalkyl include, but are not limited to, dibromomethyl, dichloromethyl, bromochloromethyl and trifluoromethyl.

The term "hydroxyalkyl" embraces linear or branched alkyl groups having one to about ten carbon atoms, any one of which may be substituted with one or more hydroxyl groups. The terms "alkenyl" and "alkynyl" embraces linear or branched radicals having two to about twenty carbon atoms, preferably two to about ten carbon atoms, and containing at least one carbon-carbon double- or triple-bond.

By $C_2$-$C_6$ alkenyl is meant a univalent linear or branched aliphatic radical having at least one double-bond or a plurality of bonds either adjacent, such as allene-type structures, or in conjugation or separated by several saturated carbons. Examples of alkenyl groups include, but are not limited to, ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl.

By $C_2$-$C_6$ alkynyl is meant a univalent linear or branched radical having at least 1 triple-bond. Examples of $C_2$-$C_6$ alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl.

The terms "cycloalkenyl" and "cycloalkynyl" embrace cyclic radicals having three to about ten ring carbon atoms including, at least one double- or triple-bond involving, respectively, adjacent ring carbons. The term "alkoxyl" embraces linear or branched oxy-containing radicals each having alkyl portions of one to about ten carbon atoms, such as a methoxyl group. The "alkoxyl" or "alkoxyalkyl" radicals may be further substituted with one or more halogen atoms, such as fluorine, chlorine or bromine, to provide haloalkoxyl or haloalkoxyalkyl groups. The term "heteroaryl" embraces aromatic ring systems containing one, two or three hetero atoms selected from oxygen, nitrogen and sulfur in a ring system having five, six or seven ring members. Examples of heteroaryl groups include, but are not limited to, thienyl, furanyl, pyridinyl, thiazolyl, pyrimidyl and isoxazolyl.

Pharmaceutically acceptable salts useful in the present invention include compounds capable of forming a salt, for example, at the nitrogen atom on the ring and which are bio-compatible and are well known to those skilled in the art. Examples of pharmaceutically acceptable salts include, but are not limited to, oxalates, citrates, tartrates, hydrochloride salts and the like, since the compounds contain basic nitrogen atoms, such salts can be acid addition salts or quaternary ammonium salts with 1 or more $C_1$-$C_6$ alkyl or cycloalkyl groups.

The compounds and compositions of the present invention are useful in treating pain.

By pain is meant acute and chronic pain, due to illness, trauma or associated with inflammation or postoperative recovery.

All percentages are by weight unless otherwise stated.

EXAMPLE 1

Isolation of Epibatidine

Skins from 750 *Epipedobates tricolor* from southwestern Ecuador were minced and extracted by trituration three times with methanol (total volume 1.5 L). After concentration of the methanol extract in vacuo to 500 mL and dilution with an equal volume of water, alkaloids were extracted three times into equal volumes of chloroform. The chloroform-soluble alkaloids were then extracted four times into one-half volumes of 0.1 N HCl. The combined 0.1 N HCl solutions were adjusted to pH 9 with 1 N aqueous ammonia, followed by extraction of alkaloids three times into equal volumes of chloroform. The combined chloroform solutions were dried over sodium sulfate and concentrated in vacuo to dryness to yield 80 mg of crude alkaloids. Sixty milligrams of crude alkaloids from *Epipedobates tricolor* were dissolved in 0.5 mL of chloroform and applied to a prepacked silica gel 60 column (Merck 1.0×24 cm) and eluted with 500 mL of chloroform-methanol-aqueous 6 N ammonia (800:10:0.1) and then with 1 L of chloroform-methanol-aqueous ammonia (1000:100:0.2). Five-milliliter fractions were collected. Fractions 108–111 contained the bulk of the alkaloid epibatidine that elicited the Straub-tail reaction in mice. The estimated recovery of Straub-tail equivalents from the column was about 40%. Fraction 108 in methanol was concentrated to 0.4 mL and further purified by HPLC on Partisil PXS 10/25 PAC with a solvent of acetonitrile-0.01 M $(NH_4)_2CO_3$ at 4 mL/min. Fractions of 0.5 mL were extracted with chloroform, the chloroform was dried over $Na_2SO_4$ and evaporated. Fraction 4 contained almost exclusively epibatidine based upon thin-layer and gas chromatographic analysis and was used for biological testing. Fraction 3 contained substantial amounts of epibatidine, along with other alkaloids.

EXAMPLE 2

Preparation of N-Acetylepibatidine

A solution of epibatidine (~300 μg) in 1 ml of $CH_3OH$ was evaporated and treated with 2 drops of acetic anhydride for 2 hrs. at room temperature, then saturated $NaHCO_3$ was added and the aqueous solution extracted with several one drop portions of EtOAc. The EtOAc layer was extracted with three 200 μl portions of 0.1 N HCl to remove any contaminating amines, dried and evaporated to dryness with a nitrogen stream. The resulting N-acetylepibatidine was homogeneous by gas chromatographic analysis and was obtained in near quantitative yield.

EXAMPLE 3

Synthesis of (±) Epibatidine (8)

The synthesis of epibatidine is shown in Scheme 1. 3-Pyridyl-2-cyclohexa-1,3-diene (1) prepared from cyclohexane-1,2-dione by the steps of Scheme 2 is reacted with tertiary butylnitroso-formate (2) in methylene chloride to provide the Diels-Alder Adduct 3. Reagent 2 is generated in situ from tertiary-butyloxycarbonylhydroxylamine and tetraethylammonium periodate. Adduct 3 (one of the two regioisomers is shown; both produce the same cyclized product 6) is hydrogenated with a 5% palladium-on-charcoal catalyst in methanol to the amino alcohol derivative 4. The amino alcohol 4 is then treated with thionyl chloride in pyridine to give the chloro amide 5 which is cyclized with base-treatment to give 6. Free radical chlorination of 6 (carbon tetrachloride, UV light source) provides 7, which on deblocking with trifluoroacetic acid in methylene chloride gives (±) epibatidine (8).

Scheme 1

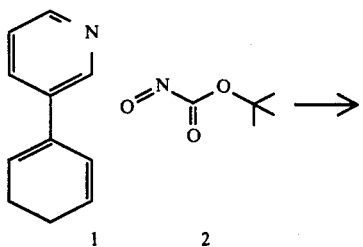

1        2

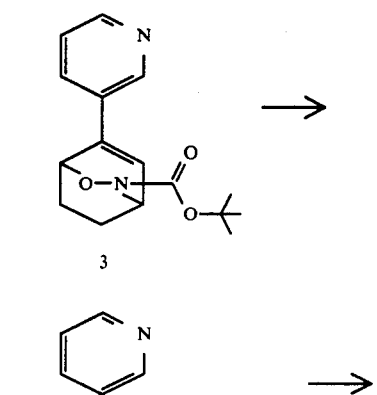

3

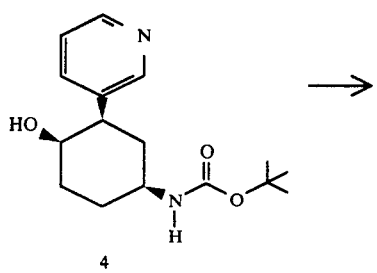

4

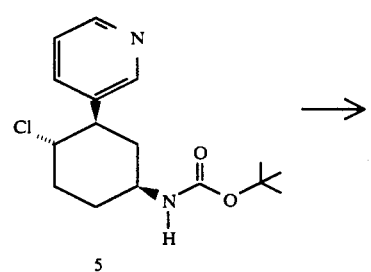

5

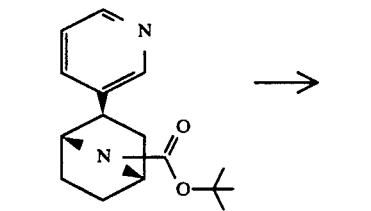

6

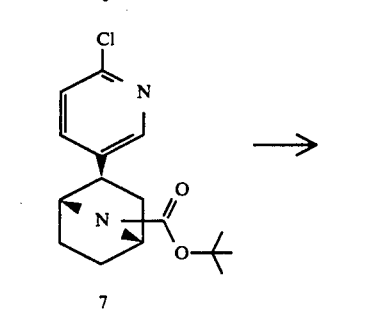

7

-continued
Scheme 1

8

As shown in Scheme 2, cyclohexane-1,2-dione is converted to 2-methoxy-cyclohex-2-enone (9) with trimethyl orthoformate and acid, and reacted with the Grignard derivative from 3-bromopyridine, 3-pyridylmagnesium bromile, in tetrahydrofuran to produce 10, which is dehydrated with phosphorous oxychloride in pyridine and hydrolyzed with dilute aqueous hydrochloric acid to give 11. Compound 11 is reduced with sodium borohydride in methanol containing cerium chloride to the allylic alcohol 12, which is dehydrated with phosphorous oxychloride in pyridine at 0° C. to give 1.

Scheme 2

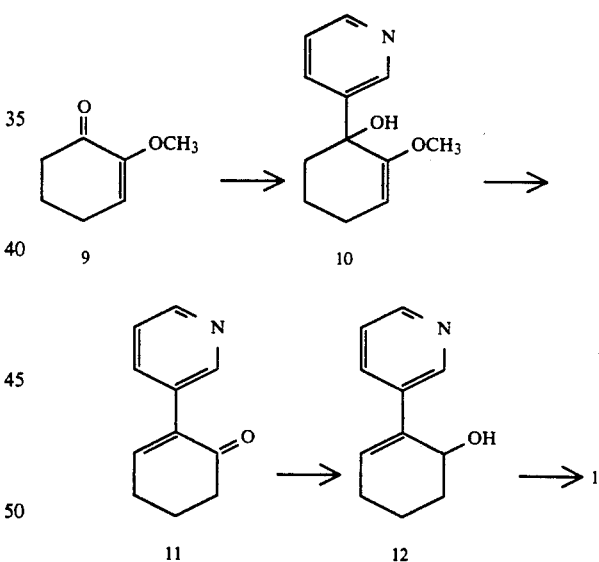

When phenylmagnesium bromide (a) or phenyllithium (b) is used in place of 3-pyridylmagnesium bromide, the phenylcarbinol enol ether 13 arises (Scheme 3). This is refluxed with acetic anhydride (c) or dehydrated with phosphorous oxychloride and pyridine (d) and hydrolyzed with aqueous hydrochloric acid (e) to give 2-phenyl-2-cyclohexenone (14). Reduction of 14 with sodium borohydride and cerium chloride in methanol (f) provides the allylic alcohol 15 which is dehydrated (d) to 2-phenyl-1,3-cyclohexadiene 16. Reaction of 16 with tertiary butyl nitrosoformate (2) as in Scheme 1, provides the Diels-Alder cycloadduct 17, which can be converted in four steps to (±) exo-2-phenyl-7-azabicyclo[2.2.1]heptane (18), the phenyl analog of epibatidine.

Scheme 3

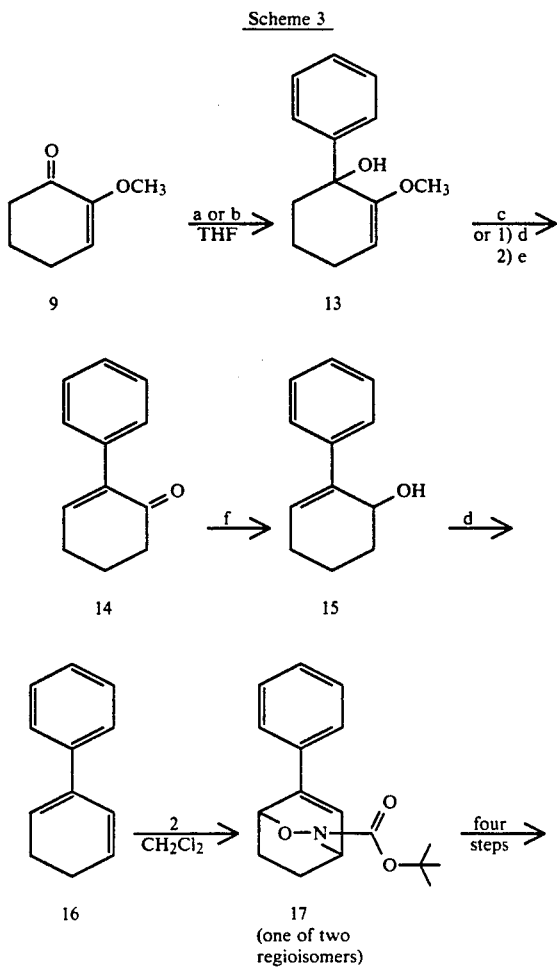

Scheme 4

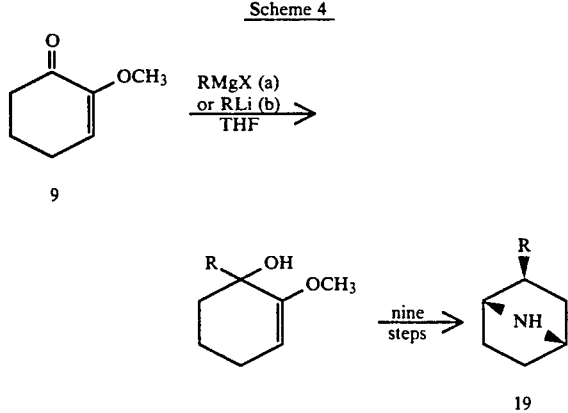

R = phenyl (a or b)
  = substituted phenyl (a or b)
  = cyclohexyl (a)
  = n-pentyl (a)
  = 3-pyridyl (a)
  = 2-thienyl (a)
  = 3-thienyl (a)
  = 2-furanyl (b)
  = various alkyl, cycloalkyl, aryl, heteroaryl, alkylaryl (a or b)

If instead of a) or b) above, 2-or 3-thienylmagnesium bromide or 2-lithiofuran is used, the analogous exo 2-(2-thienyl)-, 2-(3-thienyl)-, or 2-(2-furanyl)-7-azabicyclo-[2.2.1]heptanes (19) are produced (See Scheme 4).

Scheme 5

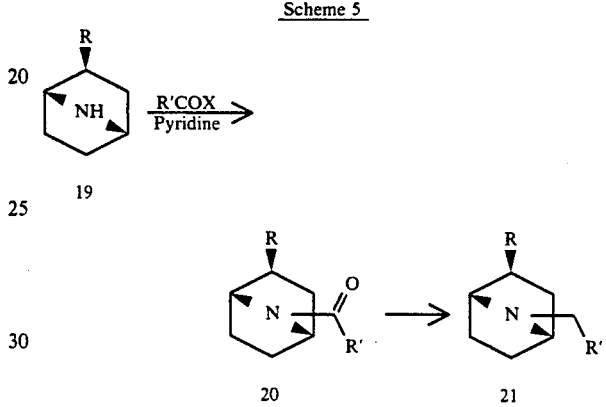

X = Cl
  = OCOR'
R' = methyl
   = vinyl
   = allyl
   = propargyl
   = n-pentyl
   = cyclohexyl
   = phenyl
   = phenetyl The exo 2-alkyl, 2-cycloalkyl or 2-aryl-substituted 7-azabicyclo[2.2.1]heptanes (19) can be N-acylated to amides (20) with a variety of acyl chlorides or acid anhydrides (see Scheme 5) as described for the conversion of epibatidine to N-acetyl epibatidine (see Example 2 above). These in turn can be reduced to N-alkyl, N-cycloalkylmethylene, or N-arylmethylene-2-substituted 7-azabicyclo [2.2.1]heptanes (21) using lithium aluminum hydride in tetrahydrofuran.

Biological Data

The assay of analgetic activity of epibatidine and comparison with morphine was conducted by a standard procedure [Eddy N.B. and Leimbach, D., J. Pharmacol. Exo. Therap. 107, 385–393, 1953]. NIH mice were dropped onto a hot plate maintained at 55° C. and the reaction time was determined. The criterion for a reaction was kicking the hind leg, attempting to jump out, or shaking a foot and turning and licking it. Reaction time for each mouse was determined at least twice before and 5, 10, 20, 30, 45 and 60 min after administration of compound. An analgetic effect was significant if the reaction times over the 60 min assay exceeded the values calculated based on preinjection time by 300 sec. A range of concentrations of a compound was used to determine the $ED_{50}$, i.e., the dose at which 50% of the mice would show a significant analgetic effect.

Analgetic activity also was apparent for epibatidine in the Nilsen assay [Nilsen, P.L., Acta Pharmacol. Toxicol. 18, 10-22, 1961].

TABLE 1

Comparison of Activity of Morphine and Epibatidine as Analgetics.

| | $ED_{50}$ Dose for Hot Plate Analgesia | Effect of Naloxone (5 mg/kg sc) |
|---|---|---|
| Morphine | 1 mg/kg sc | Blockade of Analgesia |
| Epibatidine | 0.005 mg/kg sc | No effect |

The Straub-tail reaction was assayed by a standard procedure [Aceto, M.D., et.al., Brit. J. Pharmacol. 36, 225–239, 1969]. Briefly the degree of Straub-tail reaction was observed after subcutaneous (sc) injection of doses of morphine and epibatidine and the dose required for a greater than 45° arch of tail was determined. A dose of 10 mg/kg of morphine was required, while a dose of 20 μg/kg of epibatidine elicited a comparable Straub-tail reaction. Naloxone at 5 mg/kg administered 20 min prior to either morphine or epibatidine prevented the Straub-tail reaction to 10 mg/kg morphine, but only slightly reduced the Straub-tail reaction to 20 μg/kg epibatidine.

The affinity of morphine and epibatidine for opioid-binding sites in guinea pig brain preparations was conducted by a standard procedure [Pert, C.P. and Snyder, S., Mol. Pharmacol., 10. 868–879, 1974]. Briefly, cerebral tissue from brains of male Hartley guinea pigs was homogenized in 10 volumes of ice-cold 50 mM Tris-HCl buffer (pH 7.4) for 20 sec. in a Polytron homogenizer at 3000 rpm. After centrifugation at 18,000 G for 10 min., the pellet was reconstructed to the same volume in Tris buffer. Aliquots of the suspension (1.9 ml) were incubated with 1 nM [3H]dihydromorphine and various concentrations of morphine or epibatidine in a final volume of 2 ml for 30 min. at 25° in the dark. Samples were chilled to 0° and filtered through glass fiber filters, followed by two washes with 5 ml of ice cold Tris buffer. Radioactivity retained on the filter was determined with a liquid scintillation counter. Nonspecific binding of [³H]dihydromorphine was determined in the presence of 100 nM naloxone. Morphine had an $IC_{50}$ of 1.1 nM, while epibatidine was nearly inactive with an $IC_{50}$ of 8,800 nM.

Embraced within this invention would be pharmaceutical compositions consisting of the epibatidine-class compound in association with one or more pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in an analgetic dose effective for the treatment intended. Therapeutically effective analgetic doses of the compounds of the present invention required to prevent or arrest the progress of the medical condition will be readily ascertained by one of ordinary skill in the art. The compounds and compositions may, for example, be administered parenterally, for example, intravascularly, intraperitoneally, subcutaneously, intramuscularly; or topically.

For oral administration, the pharmaceutical compositions may be in the form, for example, of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline or dextrose solutions or water may be used as a suitable carrier. A suitable dose can be administered, in multiple sub-doses per day. These sub-doses may be administered in unit dosage forms.

By analgetic effective amount is meant the dosage regimen for treating chronic or acute pain with the compounds and/or compositions of this invention and would be selected in accordance with a variety of factors, including the type, age, weight, sex and medical condition of the patient, the severity of the disease, the route of administration, and the particular compound employed. An analgetic effective amount would be considered between from about 0.1 to 20 μg/kg body weight per parenteral dose. A preferred dose would be from about 1–6 μg/kg body weight per parenteral dose.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations of parenteral administration may be in the form of aqueous or non-aqueous isotonic sterile injectable solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A purified and isolated compound having the formula:

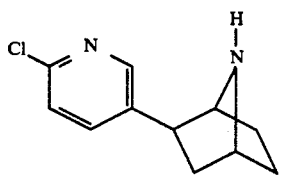

or a pharmaceutically acceptable salt thereof.

2. A compound having the formula:

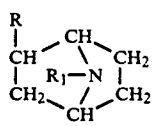

wherein $R_1$ is selected from the group consisting of H, $C_1$-$C_6$ alkyl, $C_3$-$C_9$ cycloalkyl, $C_1$-$C_7$ acyl, $C_4$-$C_9$ cycloalkylalkyl, $C_1$-$C_6$ haloalkyl, $C_2$-$C_6$ alkenyl, $C_2$-$C_6$ alkynyl, $C_1$-$C_6$ hydroxyalkyl, and $C_3$-$C_8$ cycloalkenyl; and wherein R is pyridyl, which is unsubstituted or substituted with one or more substituents selected from the group consisting of hydroxyl, $C_1$-$C_6$ alkyl, $C_2$-$C_6$ alkenyl, $C_2$-$C_6$ alkynyl, $C_1$-$C_6$ alkoxyl, halo, $C_1$-$C_6$ haloalkyl, amino, $C_1$-$C_6$ alkylamino, $C_2$-$C_{10}$ dialkylamino, and sulfonamido; or a pharmaceutically acceptable salt thereof; with the proviso that R is not 6-chloro-3-pyridyl when $R_1$ is H.

3. The compound according to claim 2, wherein R is 6-chloro-3-pyridyl and $R^1$ is $CH_3C(O)$— or a pharmaceutically acceptable salt thereof.

4. An analgetic composition which comprises an effective analgetic amount of a compound according to claim 1 and a pharmaceutically acceptable carrier.

5. An analgetic composition which comprises an effective analgetic amount of a compound according to claim 2 and a pharmaceutically acceptable carrier.

6. A method of treating pain which comprises administering to a host in need thereof, an effective amount of a compound having the formula:

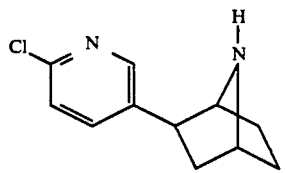

or a pharmaceutically acceptable salt thereof.

7. A method of treating pain which comprises administering to a host in need thereof, an effective amount of a compound having the formula:

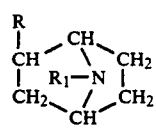

wherein $R_1$ is selected from the group consisting of H, $C_1$-$C_6$ alkyl, $C_3$-$C_9$ cycloalkyl, $C_1$-$C_7$ acyl, $C_4$-$C_9$ cycloalkylalkyl, $C_1$-$C_6$ haloalkyl, $C_2$-$C_6$ alkenyl, $C_1$-$C_6$ alkynyl, $C_1$-$C_6$ hydroxyalkyl, and $C_3$-$C_8$ cycloalkenyl; and wherein R is pyridyl, which is unsubstituted or substituted with one or more substituents selected from the group consisting of hydroxyl, $C_1$-$C_6$ alkyl, $C_2$-$C_6$ alkenyl, $C_2$-$C_6$ alkynyl, $C_1$-$C_6$ alkoxyl, halo, $C_1$-$C_6$ haloalkyl, amino, $C_1$-$C_6$ alkylamino, $C_2$-$C_{10}$ dialkylamino, and sulfonamide; or a pharmaceutically acceptable salt thereof; with the proviso that R is not 6-chloro-3-pyridyl when $R_1$ is H.

* * * * *